(12) United States Patent
Wei

(10) Patent No.: US 11,826,692 B2
(45) Date of Patent: Nov. 28, 2023

(54) WASTE GAS PURIFICATION SYSTEM

(71) Applicant: Jung-Tsung Wei, Tainan (TW)

(72) Inventor: Jung-Tsung Wei, Tainan (TW)

( * ) Notice: Subject to any disclaimer, the term of this patent is extended or adjusted under 35 U.S.C. 154(b) by 26 days.

(21) Appl. No.: 17/552,457

(22) Filed: Dec. 16, 2021

(65) Prior Publication Data

US 2022/0193594 A1 Jun. 23, 2022

(30) Foreign Application Priority Data

Dec. 17, 2020 (TW) .................................. 109144736

(51) Int. Cl.
*B01D 49/00* (2006.01)
*G01N 33/00* (2006.01)

(52) U.S. Cl.
CPC .......... *B01D 49/00* (2013.01); *G01N 33/0062* (2013.01); *B01D 2247/08* (2013.01)

(58) Field of Classification Search
CPC .. B01D 49/00; B01D 47/024; B01D 2247/08; B01D 46/0005; B01D 46/0036; B01D 46/42; B01D 46/4227; B01D 46/442; B01D 46/528; B01D 47/06; B01D 46/71; B01D 46/66; B01D 46/68; B01D 46/70; G01N 33/0062; F24F 8/80; B05B 15/68; B05B 14/43; F01N 3/023; F01N 3/0233
USPC .................................... 55/418–420, 351–354
See application file for complete search history.

(56) References Cited

U.S. PATENT DOCUMENTS

| | | | | |
|---|---|---|---|---|
| 3,850,373 | A * | 11/1974 | Grolitsch | ................ B05B 1/28 239/499 |
| 8,431,180 | B2 * | 4/2013 | Fritz | ................... B05B 14/437 118/712 |
| 2005/0181142 | A1 * | 8/2005 | Hirano | .................. B05B 5/0407 427/421.1 |
| 2009/0205683 | A1 * | 8/2009 | Ogata | .................... B05B 15/55 134/22.12 |
| 2011/0166708 | A1 * | 7/2011 | Herre | ..................... B05B 16/40 901/46 |
| 2019/0001249 | A1 * | 1/2019 | Hong | ..................... F24F 7/007 |

FOREIGN PATENT DOCUMENTS

| | | | |
|---|---|---|---|
| CN | 103212257 A | 7/2013 | |
| CN | 110180303 A | 8/2019 | |
| CN | 111514671 A | 8/2020 | |
| DE | 4300400 A1 * | 7/1993 | ............. B01D 46/10 |

(Continued)

OTHER PUBLICATIONS

JPH07178354A_ENG (Espacenet machine translation of Arimoto) (Year: 1995).*

(Continued)

*Primary Examiner* — Gabriel E Gitman
(74) *Attorney, Agent, or Firm* — Brooks Kushman PC.

(57) ABSTRACT

A waste gas purification system includes a gas container, a driver, a gas input unit, a gas output unit and a contaminant capturing apparatus. The gas input unit is for entrance of waste gas into the gas container, and is to be driven by the driver into movement. The gas output unit is for discharge of the waste gas out of the gas container after the waste gas is purified. The contaminant capturing apparatus is disposed in the gas container, and includes a capture device that purifies the waste gas by using an adhesive to adhere particulate matter in the waste gas.

14 Claims, 10 Drawing Sheets

(56) References Cited

FOREIGN PATENT DOCUMENTS

| EP | 1250966 A1 | * | 10/2002 | ............. B01D 46/18 |
| JP | H-07178354 A | * | 7/1995 | ............. B05B 12/08 |
| KR | 20140077494 A | * | 6/2014 | ............ B01D 46/106 |
| KR | 20180056280 A | * | 5/2018 | ......... B01D 46/0005 |
| WO | WO-2018112507 A1 | * | 6/2018 | ............. A61L 9/048 |

OTHER PUBLICATIONS

DE4300400A1_ENG (Espacenet machine translation of Schlumpf) (Year: 1993).*
KR20140077494A_ENG (Espacenet machine translation of Kim) (Year: 2014).*
KR20180056280A_ENG (Espacenet machine translation of Yoo) (Year: 2018).*
Search Report issued to PCT application No. PCT/IB2021/061755 dated Apr. 6, 2022.

* cited by examiner

WASTE GAS PURIFICATION SYSTEM

CROSS-REFERENCE TO RELATED APPLICATION

This application claims priority of Taiwanese Patent Application No. 109144736, filed on Dec. 17, 2020.

FIELD

The disclosure relates to an apparatus for processing waste gas, and more particularly to a waste gas purification system.

BACKGROUND

With the development of industries, many factories will set up an apparatus that burns fuel to create a high temperature environment for high temperature processing. Such apparatus usually uses coals or fossil fuel, which will generate a large amount of waste gas. The waste gas usually contains harmful substances such as granular pollutants, sulfur oxides, hydroxides, etc. In addition to those used in factories, other machines such as transportation vehicles may also generate waste gas during operation. In order to prevent the waste gas generated during the operation of these apparatuses or machines from being directly emitted to the atmosphere and creating pollution, environmental protection regulations stipulate emission standards with respect to the waste gas or smoke generated by such an apparatus or machine, so industries usually set up a waste gas purification system on the apparatus or machine to purify the waste gas.

Chinese Patent Application Publication No. 103212257 discloses a conventional waste gas purification system. The conventional waste gas purification system includes a casing, and a mucus wall disposed in the casing. The casing is formed with two openings, one of which is for entrance of waste gas into the casing, and the other one of which is for discharge of the waste gas out of the casing after the waste gas is purified. The mucus wall has a surface having a silica-based polymer mucus distributed thereon in flowing state to purify the waste gas by adhering particulate matter in the waste gas. However, the conventional waste gas purification system has poor purification effect.

SUMMARY

Therefore, an object of the disclosure is to provide a waste gas purification system that can alleviate the drawback of the prior art.

According to the disclosure, the waste gas purification system includes a gas container, a driver, a gas input unit, a gas output unit and a contaminant capturing apparatus. The gas input unit is for entrance of waste gas into the gas container, and is to be driven by the driver into movement. The gas output unit is for discharge of the waste gas out of the gas container after the waste gas is purified. The contaminant capturing apparatus is disposed in the gas container, and includes a capture device that purifies the waste gas by using an adhesive to adhere particulate matter in the waste gas.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
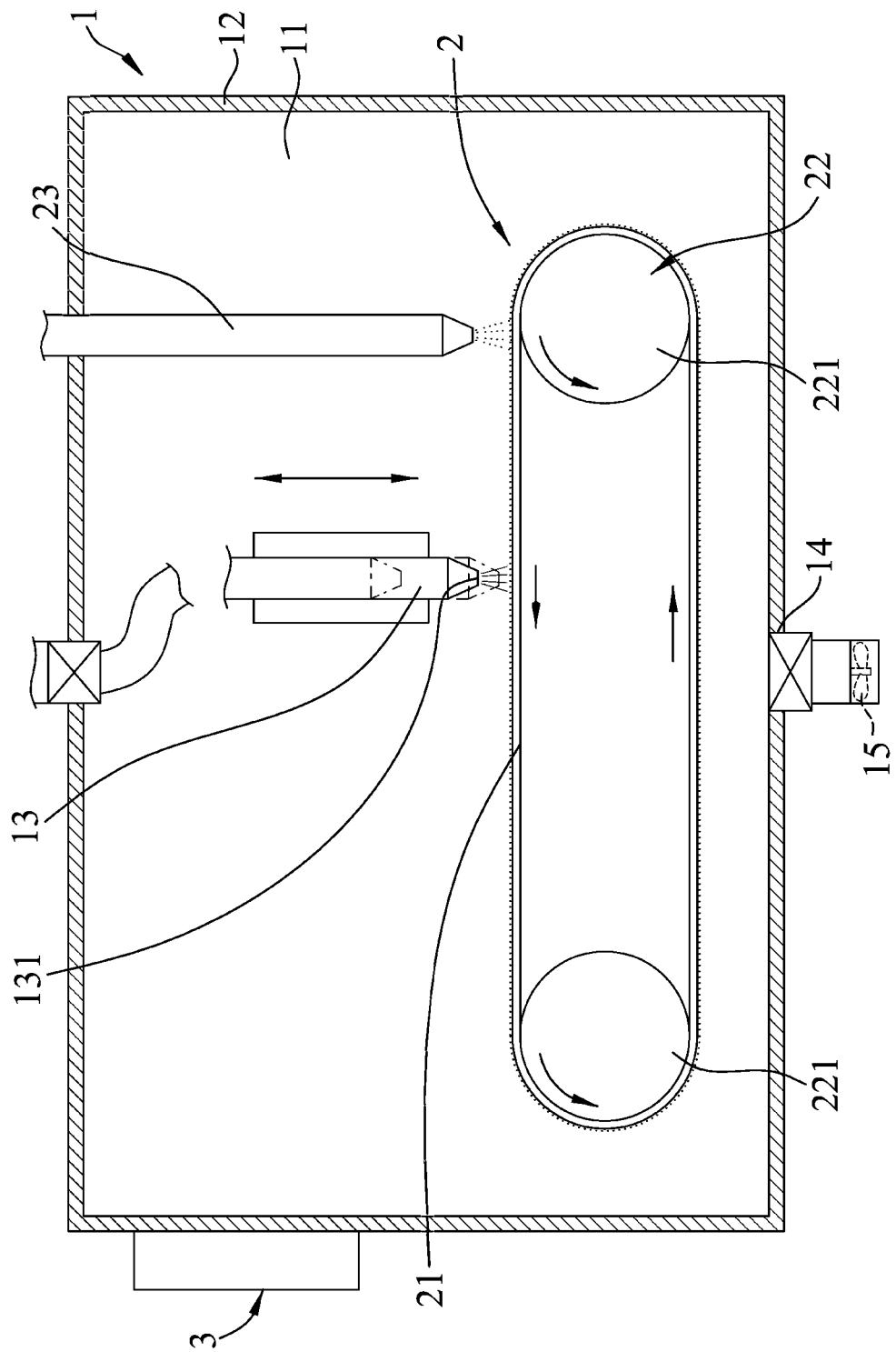
FIG. 1 is a fragmentary schematic diagram illustrating a first embodiment of a waste gas purification system according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
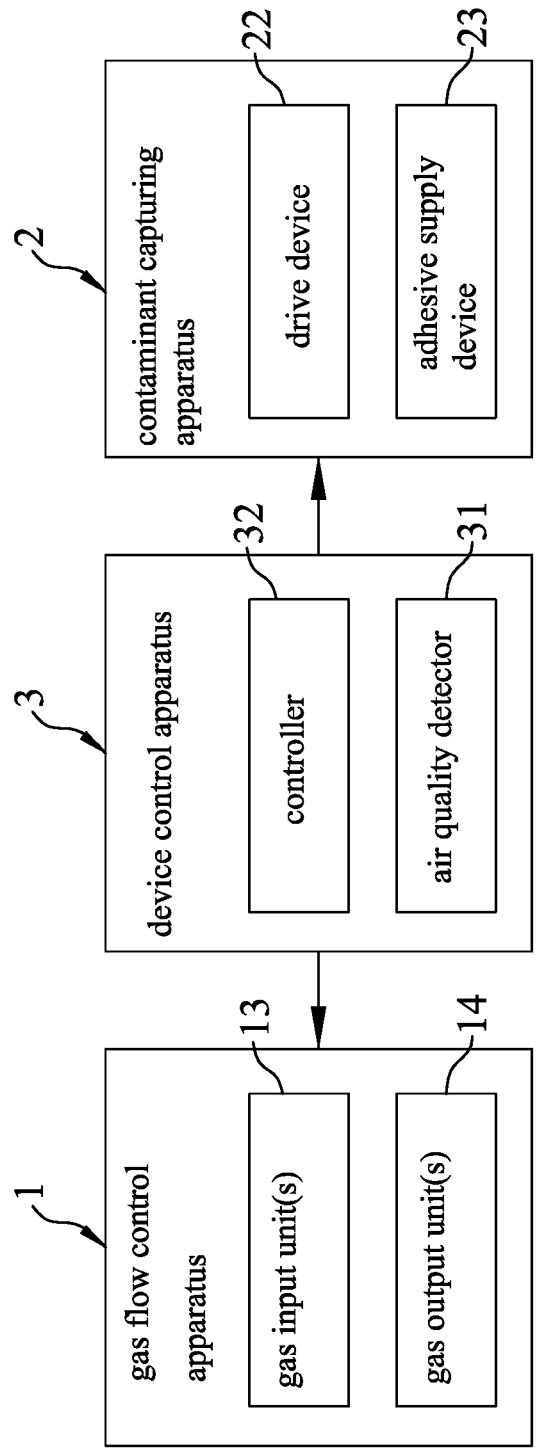
FIG. 2 is a block diagram illustrating the first embodiment.

Referring to FIGS. 1 and 2, a first embodiment of a waste gas purification system according to the disclosure is adapted to be connected to a waste gas generating apparatus (not shown) that generates waste gas, receives and purifies the waste gas from the waste gas generating apparatus, and then discharges the purified waste gas from the waste gas purification system. The waste gas purification system of this embodiment includes a gas flow control apparatus 1, a contaminant capturing apparatus 2 and a device control apparatus 3.

The gas flow control apparatus 1 includes a gas container 12 that defines a purification space 11, at least one gas input unit 13 that is to be connected to the waste gas generating apparatus for entrance of the waste gas into the purification space 11 of the gas container 12, and at least one gas output unit 14 that is for discharge of the waste gas from the purification space 11 of the gas container 12 after the waste gas is purified. In this embodiment, the gas flow control apparatus 1 includes one gas input unit 13 and one gas output unit 14, but the disclosure is not limited in this respect. In some embodiments, the gas flow control apparatus 1 may further (but not necessarily) include an exhaust fan 15 that is mounted to the gas output unit 14 for assisting in discharging the purified waste gas out of the gas container 12.

In this embodiment, the gas input unit 13 includes a nozzle that is mounted to the gas container 12, that is formed with an opening 131, and that is configured to allow for entrance of the waste gas (e.g., by injection) generated by the waste gas generating apparatus into the purification space 11 of the gas container 12 through the opening 131, continuously or intermittently. The gas output unit 14 includes an opening that is formed in the gas container 12 at an opposite side to the gas input unit 13 (e.g., the gas input unit 13 is disposed at the upper part of the gas container 12, and the gas output unit 14 is disposed at the lower part of the gas container 12 in FIG. 1), but the disclosure is not limited in this respect (i.e., it may also be that the gas input unit 13 and the gas output unit 14 are not disposed at opposite sides of the gas container 12). Each of the gas input unit 13 and the gas output unit 14 further includes a valve (not shown) that is operable to make the corresponding one of the gas input unit 13 and the gas output unit 14 open or closed.

The contaminant capturing apparatus 2 is disposed in the gas container 12, and includes a capture device 21, a drive device 22 and an adhesive supply device 23. The capture device 21 is configured to purify the waste gas by using an adhesive to adhere particulate matter in the waste gas. The drive device 22 is configured to drive the capture device 21 into continuous movement. The adhesive supply device 23 is configured to supply the adhesive to the capture device 21. In this embodiment, the drive device 22 includes two rollers 221 that are disposed below the gas input unit 13, and a motor (not shown) that is connected to and controls rotation of the rollers 221; and the capture device 21 is a belt that is trained on the rollers 221, and that runs under the gas input unit 13 when the rollers 221 rotate. The capture device 21 may be inherently sticky or inherently non-sticky. In some embodiments, the capture device 21 may be a tape (with or without a release paper) that extends from one roller 221 to another roller 221 and that runs under the gas input unit 13 when the rollers 221 rotate, a liquid adhesive in which each of the rollers 221 is partially submerged, or other suitable elements. The adhesive supply device 23 may be omitted when the capture device 21 is inherently sticky. The structure of the drive device 22 may be altered when the structure of the capture device 21 is altered.

In this embodiment, the adhesive supply device 23 continuously or intermittently sprays the adhesive onto a surface of the capture device 21 that faces the opening 131 of the gas input unit 13, and is disposed at a fixed position inside the gas container 12. In some embodiments, the adhesive supply device 23 may be driven to reciprocate or circulate parallel to the surface of the capture device 21, or to pivot about an axis parallel to the surface of the capture device 21. In addition, the adhesive supply device 23 may spread the adhesive onto the surface of the capture device 21, or may supply the adhesive to the surface of the capture device 21 in other ways. It should be noted that: (a) a number of the capture device 21 included in the contaminant capturing apparatus 2 is not limited to one, and can be two, three or more than three in other embodiments; and (b) a number of the adhesive supply device 23 included in the contaminant capturing apparatus 2 is not limited to one, and can be two, three or more than three in other embodiments.

The device control apparatus 3 includes an air quality detector 31 (which may also be called air quality monitor or air quality detection system in the market), a controller 32 and a driver 33. The air quality detector 31 is disposed in the purification space 11 defined by the gas container 12, and is configured to detect air quality of the waste gas (e.g., concentration of the particulate matter in the waste gas) in the purification space 11, and to generate an air quality signal that indicates the air quality of the waste gas as detected thereby. The controller 32 is communicatively connected to the air quality detector 31, the driver 33, the gas input unit 13, the gas output unit 14 and the drive device 22, and is to receive the air quality signal from the air quality detector 31. The driver 33 is connected to the gas input unit 13. The controller 32 is configured to control operations of the gas input unit 13, the gas output unit 14, the drive device 22 and the driver 33 based on the air quality of the waste gas as indicated by the air quality signal.

The controller 32 is configured to control an operation state (i.e., to be open or closed) of the gas input unit 13, and a gas flow in the gas input unit 13 (including a gas flow rate in the gas input unit 13, and a length of time the gas input unit 13 allows for entrance of the waste gas into the gas container 12). When the gas input unit 13 is temporarily closed, no new waste gas would enter the purification space 11 to disturb the particulate matter suspending in the purification space 11, and there would be sufficient time for the particulate matter suspending in the purification space 11 to fall onto the surface of the capture device 21, thereby promoting purification effect. The controller 32 is configured to further control an operation state (i.e., to be open or closed) of the gas output unit 14, and an operation speed of the drive device 22 (e.g., the rotational speed of the rollers 211 as shown in FIG. 1). The controller 32 is configured to further control the driver 33 to drive the gas input unit 13 into movement. In this embodiment, the gas input unit 13 is driven to move in such a way that a distance therefrom to the surface of the capture device 21 is variable. The gas input unit 13 may reciprocate in a straight line that is not parallel to the surface of the capture device 21 (e.g., reciprocate in a straight line that is perpendicular to the surface of the capture device 21 in FIG. 1), may reciprocate in a curved line that is not on a plane parallel to the surface of the capture device 21, may circulate not on a plane parallel to the surface of the capture device 21, or may pivot about an axis that is not perpendicular to the surface of the capture device 21. The driver 33 is a motorized slide that is disposed in the gas container 12 in this embodiment, but may be a linear actuator, a pneumatic cylinder or other elements in other embodiments. In some embodiments, the controller 32 may be further communicatively connected to the adhesive supply device 23, and may further control operation of the adhesive supply device 23.

During operation, the controller 32 controls the drive device 22 to drive the capture device 21 into continuous movement. The adhesive supply device 23 sprays the adhesive onto the surface of the capture device 2, so as to maintain stickiness of the adhesive on the surface of the capture device 21. The controller 32 controls the operation states of the gas input unit 13 and the gas output unit 14 to direct the waste gas into the purification space 11 and then onto the surface of the capture device 21. The adhesive on the surface of the capture device 21 adheres the particulate matter in the waste gas to purify the waste gas. The air quality detector 31 detects the air quality of the waste gas in the purification space 11, and generates the air quality signal that indicates the air quality of the waste gas as detected thereby. The controller 32 receives the air quality signal from the air quality detector 31, and controls the operations of the gas input unit 13, the gas output unit 14, the drive device 22 and the driver 33 based on the air quality signal. When determining that the air quality of the waste gas as indicated by the air quality signal is worse than a first predetermined level, the controller 32 may reduce the length of time the gas input unit 13 allows for entrance of the waste gas into the gas container 12, reduce the gas flow rate in the gas input unit 13, control the gas input unit 13 to be closed immediately, control the driver 33 to drive the gas input unit 13 to move closer to the surface of the capture device 21, or control the drive device 21 to increase the operation speed of the drive device 21 (so the rotational speed of the rollers 211 as shown in FIG. 1 may increase). When determining that the air quality of the waste gas as indicated by the air quality signal is better than a second predetermined level that represents a better air quality than that represented by the first predetermined level, the controller 32 may prolong the length of time the gas input unit 13 allows for entrance of the waste gas into the gas container 12, increase the gas flow rate in the gas input unit 13, control the driver 33 to drive the gas input unit 13 to move away from the surface of the capture device 21, control the drive device 21 to reduce the operation speed of the drive device 21 (so the rotational speed of the rollers 211 as shown in FIG. 1 may decrease), or control the drive device 21 to stop operating immediately (so the rollers 211 as shown in FIG. 1 no longer rotate). As such, the particulate matter in the waste gas can be effectively captured without incurring excessive waste material from use of the capture device 21. When determining that the air quality of the waste gas as indicated by the air quality signal conforms to an emission standard, the controller 32 controls the gas output unit 14 to be open for discharging the purified waste gas out of the gas container 12.

In some embodiments, the controller 32 may generate, based on the air quality of the waste gas when the waste gas initially entered the gas container 12 and the air quality of the waste gas when the waste gas is being discharged out of the gas container 12, air pollution indices of the waste gas before and after purification by the contaminant capturing apparatus 2, and output an air pollution index (API) signal that indicates these air pollution indices. The device control apparatus 3 may further include a display (not shown) that is communicatively connected to the controller 32 to receive the API signal, and that displays the air pollution indices of the waste gas before and after purification according to the API signal, so users can become aware of improvement on the air quality of the waste gas.

Figure 3:
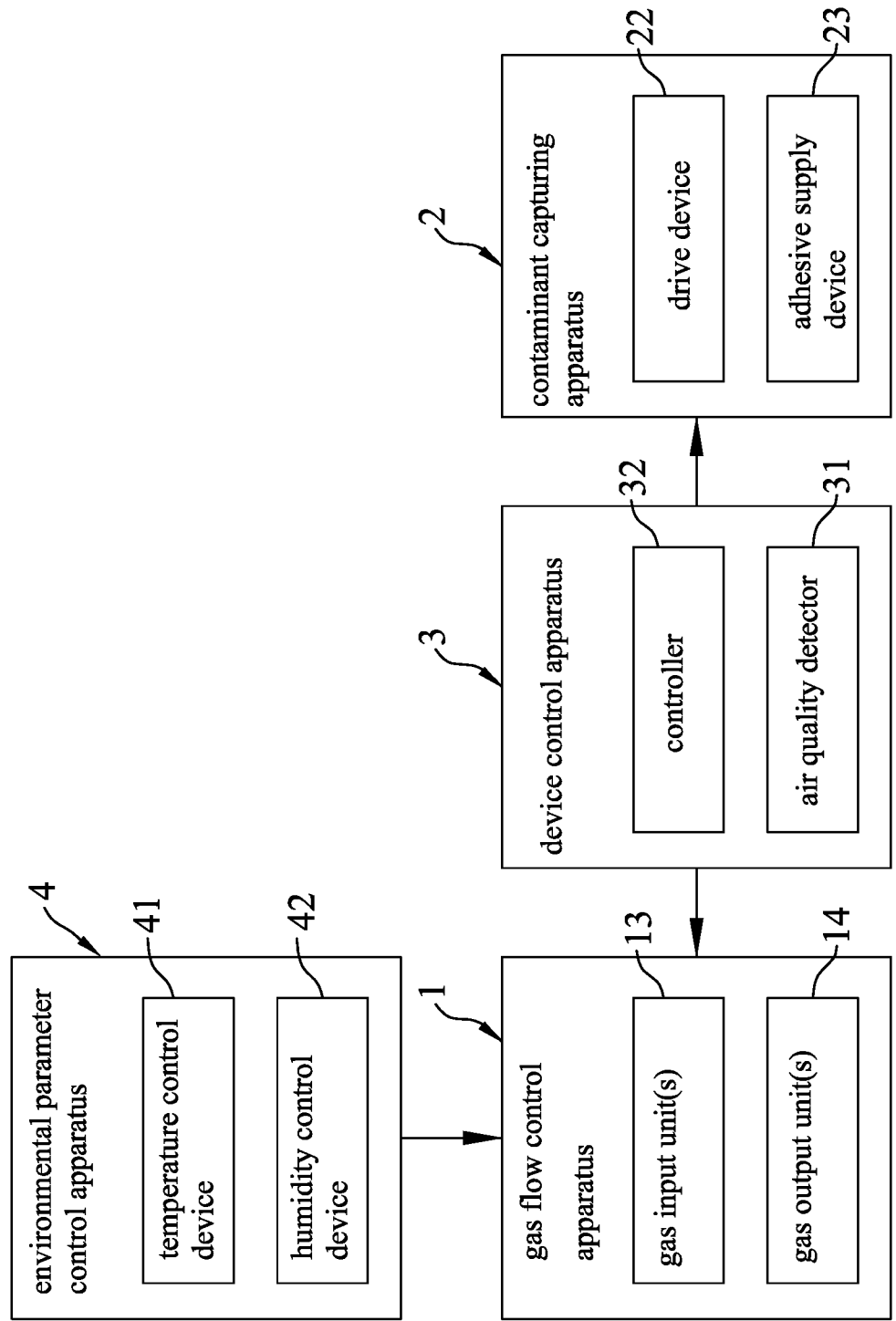
FIG. 3 is a block diagram illustrating a second embodiment of the waste gas purification system according to the disclosure.

Referring to FIG. 3, a second embodiment of the waste gas purification system according to the disclosure is similar to the first embodiment, and differs from the first embodiment in that the waste gas purification system further includes an environmental parameter control apparatus 4. The environmental parameter control apparatus 4 includes a temperature control device 41 and a humidity control device 42. The temperature control device 41 is disposed to adjust the waste gas to having a predetermined temperature before the waste gas enters the gas container 12 through the gas input unit 13, and may be realized as a fan that blows wind toward a sidewall of the gas input unit 13 to lower the temperature of the waste gas in the gas input unit 13, an air conditioner that blows cold or warm air toward the sidewall of the gas input unit 13, or electric heating tubes that are embedded in the sidewall of the gas input unit 13, etc. The humidity control device 42 is disposed to adjust the waste gas to having a predetermined humidity before the waste gas enters the gas container 12 through the gas input unit 13, and may be realized as a dehumidifier and/or a humidifier. By virtue of adjusting the temperature and the humidity of the waste gas, the stickiness of the adhesive on the surface of the capture device 21 may be optimized, so as to enhance the purification efficiency of the contaminant capturing apparatus 2 adhering the particulate matter in the waste gas. In some variations of the second embodiment, the environmental parameter control apparatus 4 may use only one of the temperature control device 41 and the humidity control device 42, or may further include other devices that can adjust environmental parameters. Since positioning and structures of the devices for environmental parameter control should be known to one skilled in the art, details thereof are omitted herein for the sake of brevity.

Figure 4:
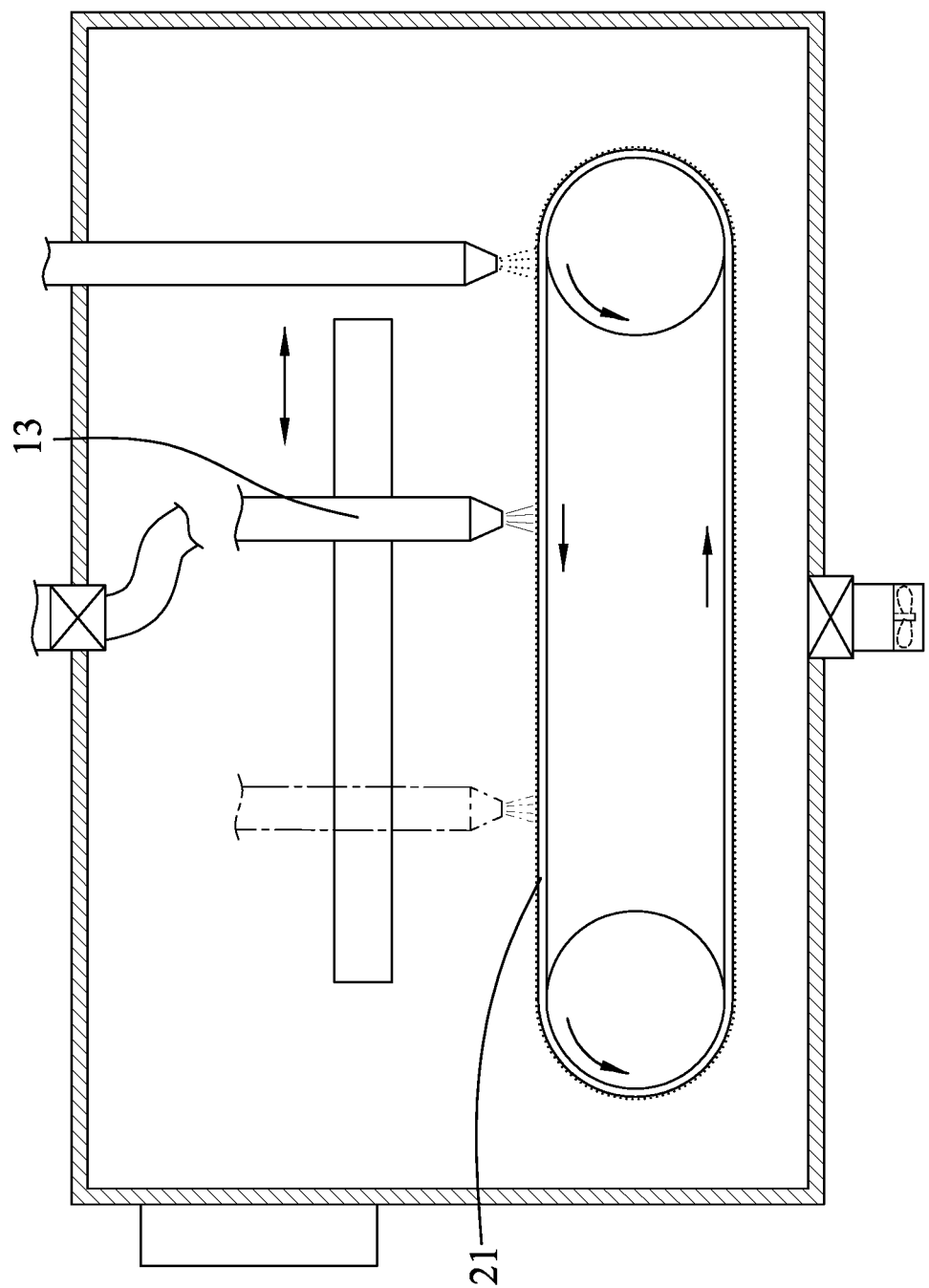
FIG. 4 is a fragmentary schematic diagram illustrating a third embodiment of the waste gas purification system according to the disclosure.

Referring to FIG. 4, a third embodiment of the waste gas purification system according to the disclosure is similar to the first embodiment, and differs from the first embodiment in that the gas input unit 13 is driven by the driver 33 to move in such a way that a position of a projection of the gas input unit 13 on the surface of the capture device 21 is variable. The gas input unit 13 may be moved in a straight line that is not perpendicular to the surface of the capture device 21 (e.g., parallel to the surface of the capture device 21 as shown in FIG. 4), or in a curved line. In some embodiments, the gas input unit 13 may be driven to move in such a way that both of the distance from the gas input unit 13 to the surface of the capture device 21 and the position of the projection of the gas input unit 13 on the surface of the capture device 21 are variable.

Figure 5:
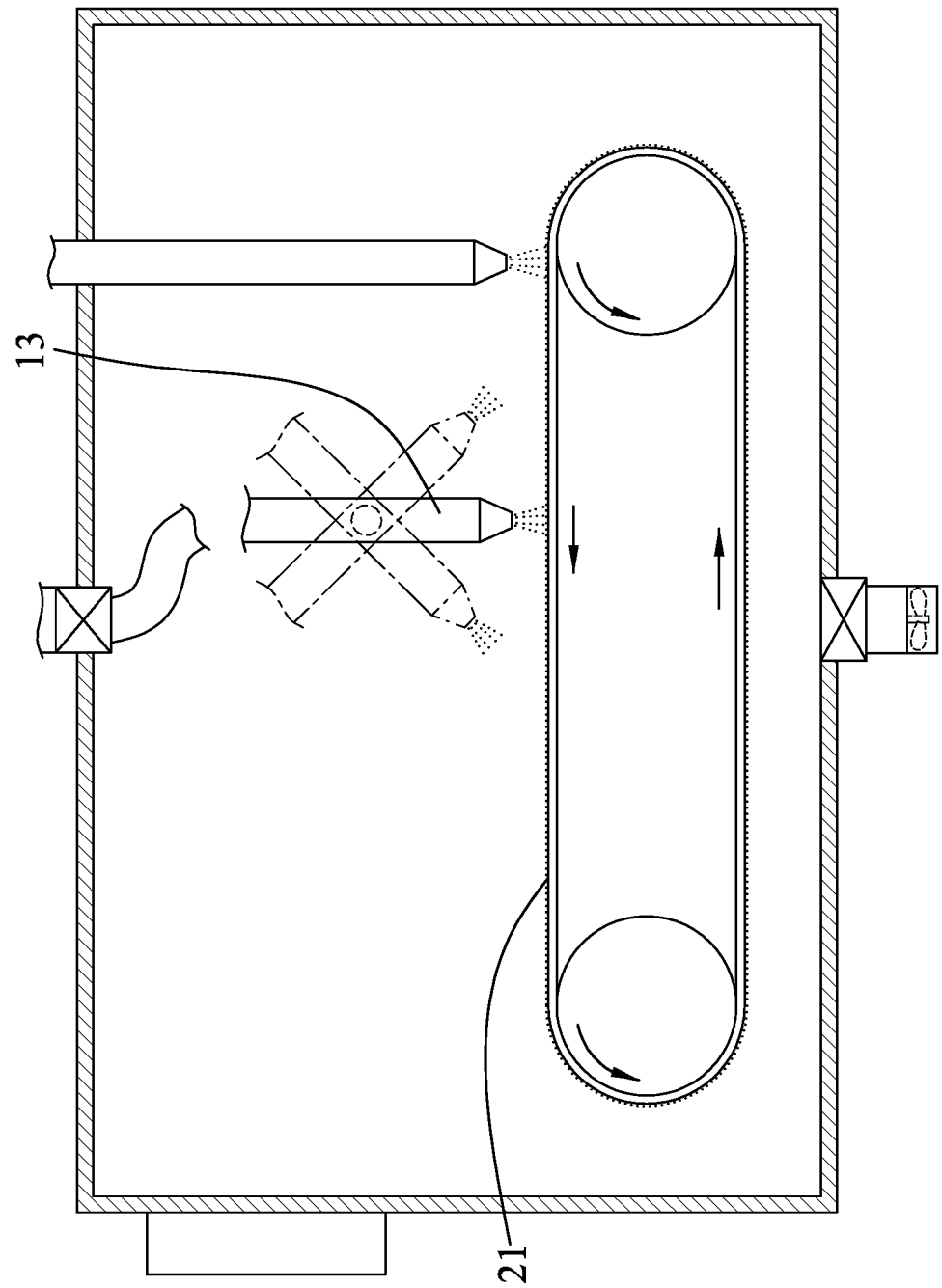
FIG. 5 is a fragmentary schematic diagram illustrating a fourth embodiment of the waste gas purification system according to the disclosure.

Referring to FIG. 5, a fourth embodiment of the waste gas purification system according to the disclosure is similar to the first embodiment, and differs from the first embodiment in that the gas input unit 13 is driven by the driver 33 to move in such a way that an angle of the gas input unit 13 with respect to the surface of the capture device 21 is variable. The driver 33 may be realized as a shaft that causes the gas input unit 13 to pivot about an axis not perpendicular to the surface of the capture device 21 (e.g., parallel to the surface of the capture device 21 as shown in FIG. 5). In some embodiments, the gas input unit 13 may be driven to move in such a way that the angle of the gas input unit 13 with respect to the surface of the capture device 21 is variable and that at least one of the distance from the gas input unit 13 to the surface of the capture device 21 or the position of the projection of the gas input unit 13 on the surface of the capture device 21 is variable.

Figure 6:
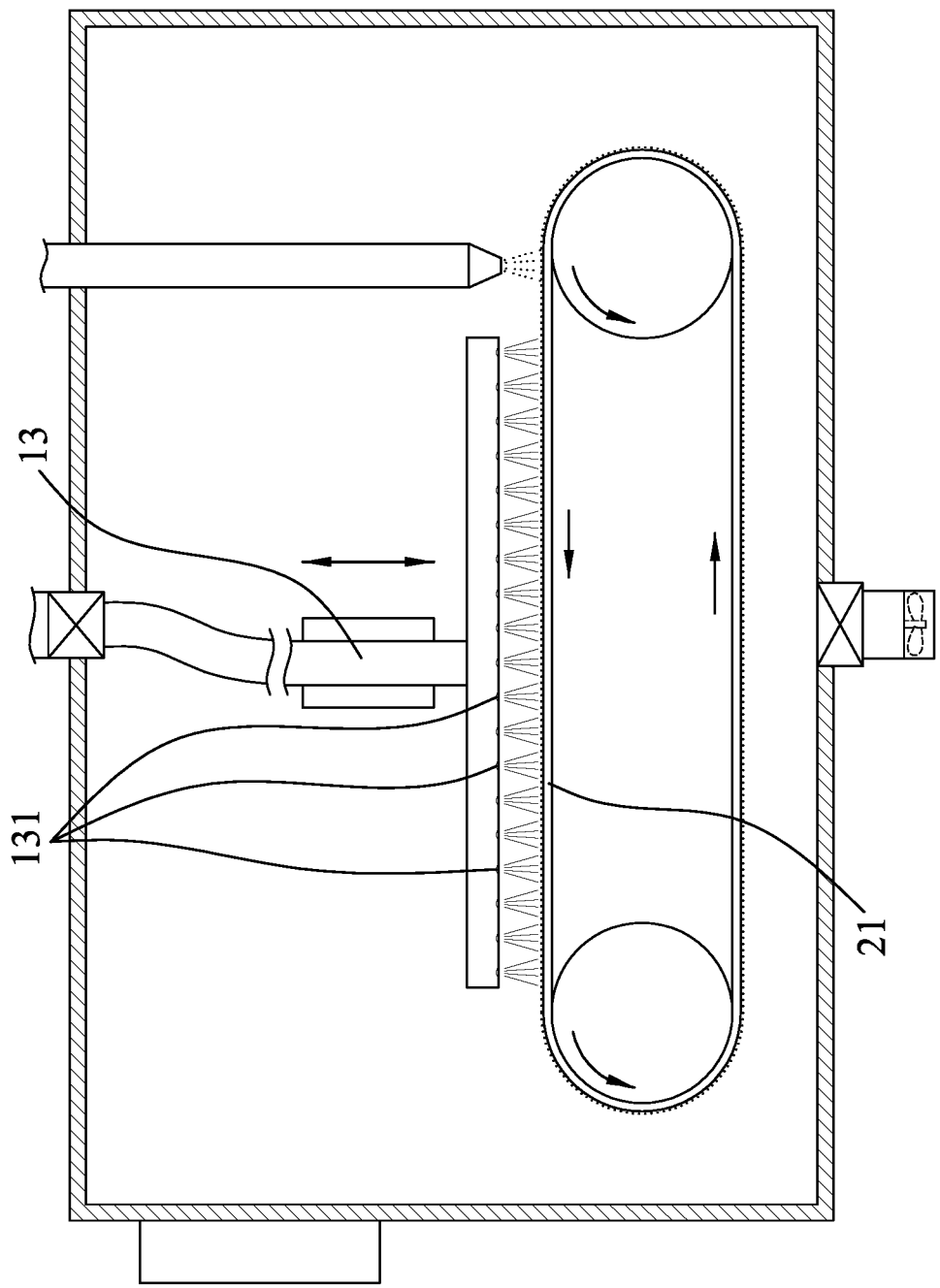
FIG. 6 is a fragmentary schematic diagram illustrating a fifth embodiment of the waste gas purification system according to the disclosure.

Referring to FIG. 6, a fifth embodiment of the waste gas purification system according to the disclosure is similar to the first embodiment, and differs from the first embodiment in that the gas input unit 13 is formed with a plurality of openings 131 facing the surface of the capture device 21, so as to increase a number of regions (and hence, an overall area) of the adhesive on the surface of the capture device 21 that are exposed to the waste gas, and thus enhance the purification efficiency.

Figure 7:
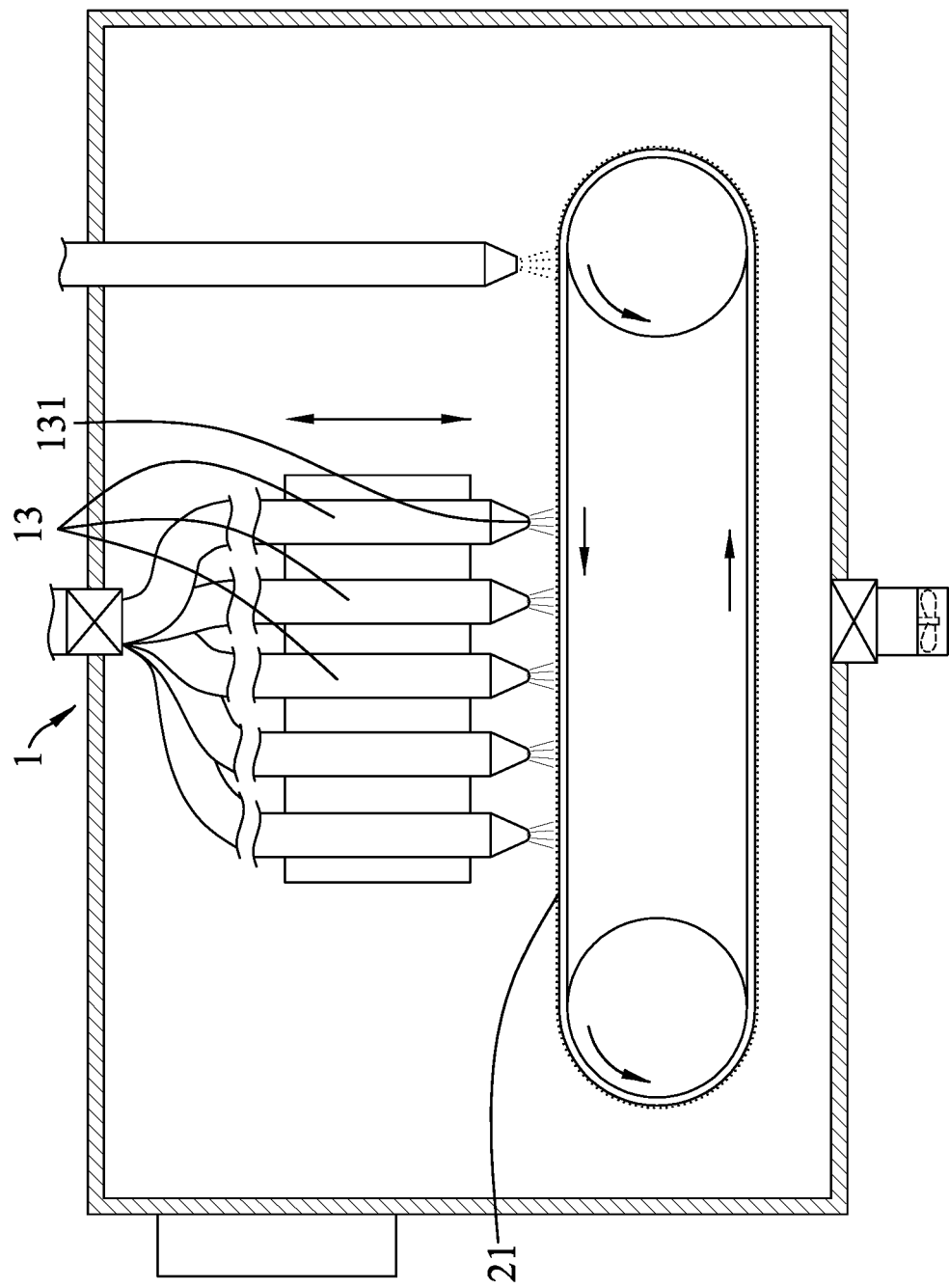
FIG. 7 is a fragmentary schematic diagram illustrating a sixth embodiment of the waste gas purification system according to the disclosure.

Referring to FIG. 7, a sixth embodiment of the waste gas purification system according to the disclosure is similar to the first embodiment, and differs from the first embodiment in that the gas flow control apparatus 1 includes a plurality of gas input units 13, and that respective openings 131 of the gas input units 13 all face the surface of the capture device 21, so as to increase a number of regions (and hence, an overall area) of the adhesive on the surface of the capture device 21 that are exposed to the waste gas, and thus enhance the purification efficiency. In some variations of the sixth embodiment, each of the gas input units 13 may be formed with a plurality of openings 131.

Figure 8:
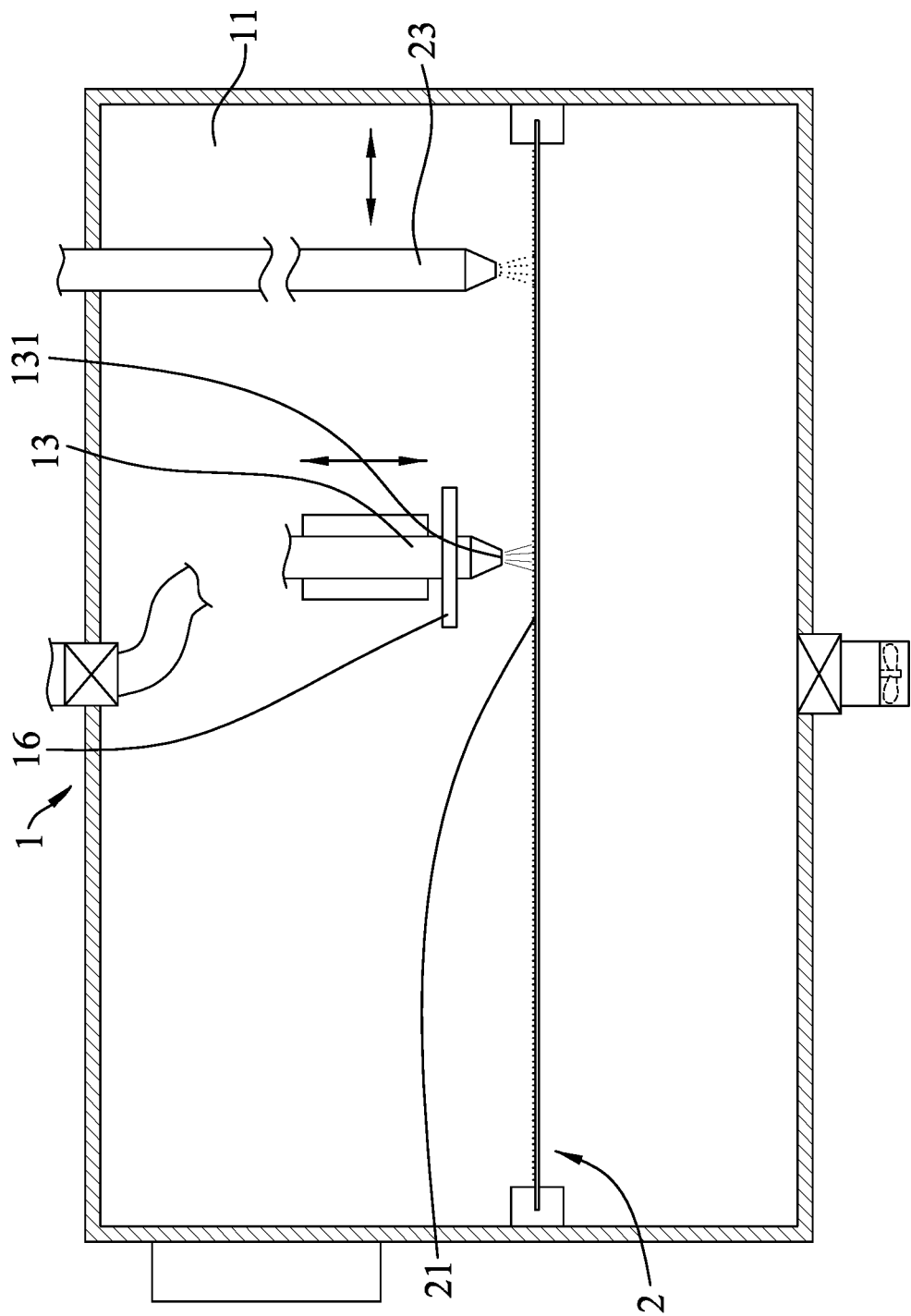
FIG. 8 is a fragmentary schematic diagram illustrating a seventh embodiment of the waste gas purification system according to the disclosure.

Referring to FIG. 8, a seventh embodiment of the waste gas purification system according to the disclosure is similar to the first embodiment, and differs from the first embodiment in that the gas flow control apparatus 1 further includes a reflector 16, and that the adhesive supply device 23 is driven into movement, and in the structure of the contaminant capturing apparatus 2. In the seventh embodiment, the contaminant capturing apparatus 2 does not include the drive device 22 as shown in FIG. 1. The capture device 21 is a band that is disposed at a fixed position below the gas input unit 13, and that may be replaced by a new one when necessary. The capture device 21 is inherently non-sticky in this embodiment, but may be inherently sticky in other embodiments. The adhesive supply device 23 reciprocates or circulates parallel to a surface of the capture device 21 that faces the opening 131 of the gas input unit 13 to spray the adhesive all over the surface of the capture device 21. The reflector 16 is mounted to the gas input unit 13 and above the opening 131 of the gas input unit 13, and extends radially-outwardly from the gas input unit 13, so the particulate matter in the waste gas that has bounced up from the surface of the capture device 21 would be returned by the reflector 16, thereby reducing a length of time the particulate matter in the waste gas suspends in the purification space 11 far from the surface of the capture device 21, and thus increasing likelihood of the particulate matter in the waste gas being captured (adhered) by the adhesive on the surface of the capture device 21. The likelihood of the particulate matter in the waste gas being captured by the adhesive on the surface of the capture device 21 can be further increased by increasing an area of the reflector 16. It should be noted that a number of the reflector 16 included in the gas flow control apparatus 1 is not limited to one, and can be two, three or more than three in other embodiments. In some variations of the seventh embodiment, the contaminant capturing apparatus 2 may have a structure identical to that of the first embodiment as shown in FIG. 1, or may have other structures.

Figure 9:
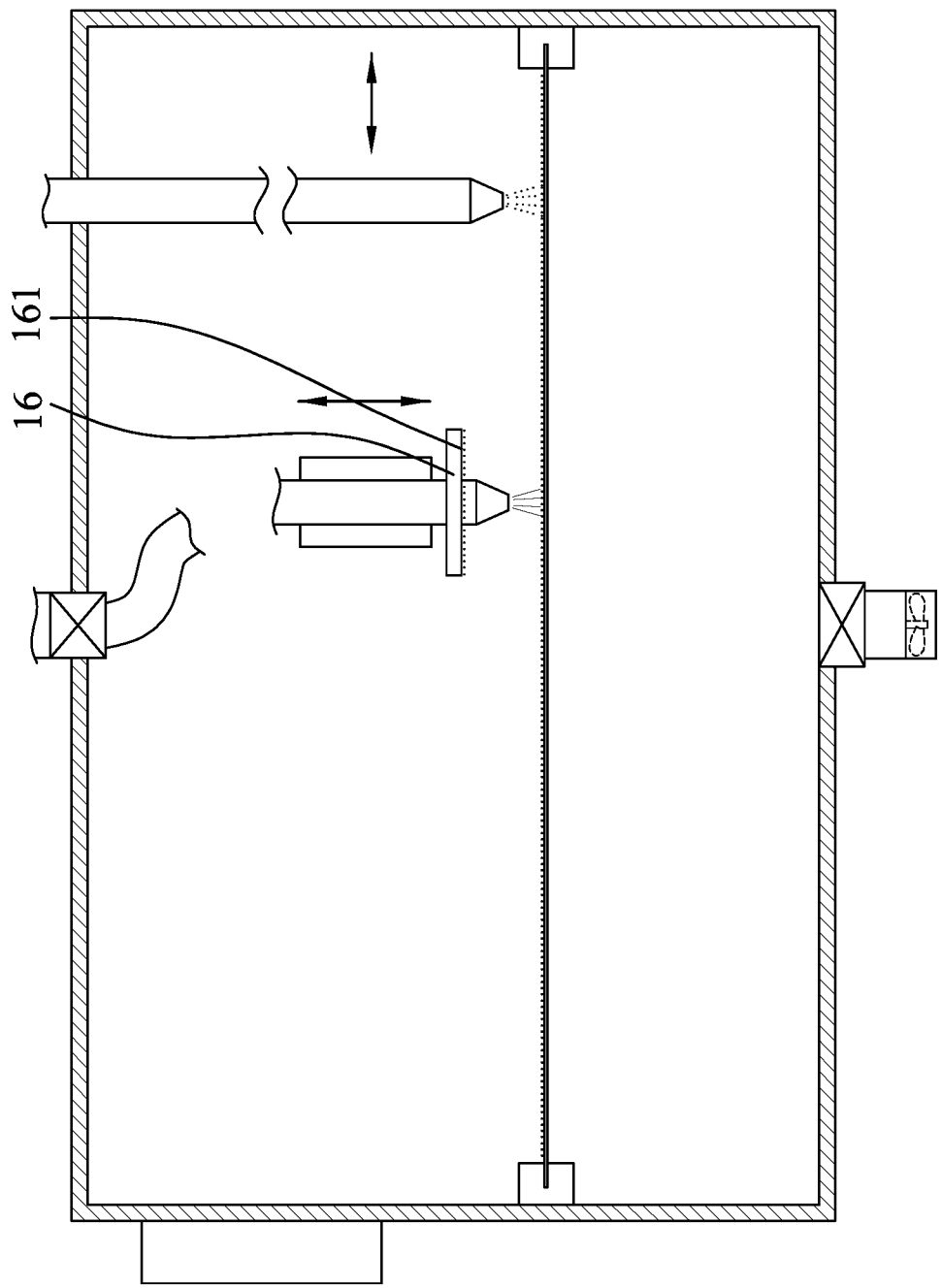
FIG. 9 is a fragmentary schematic diagram illustrating an eighth embodiment of the waste gas purification system according to the disclosure.

Referring to FIG. 9, an eighth embodiment of the waste gas purification system according to the disclosure is similar to the seventh embodiment, and differs from the seventh embodiment in that the reflector 16 has a surface 161 having adhesive distributed thereon to adhere the particulate matter in the waste gas, thereby increasing likelihood that the particulate matter in the waste gas is captured.

Figure 10:
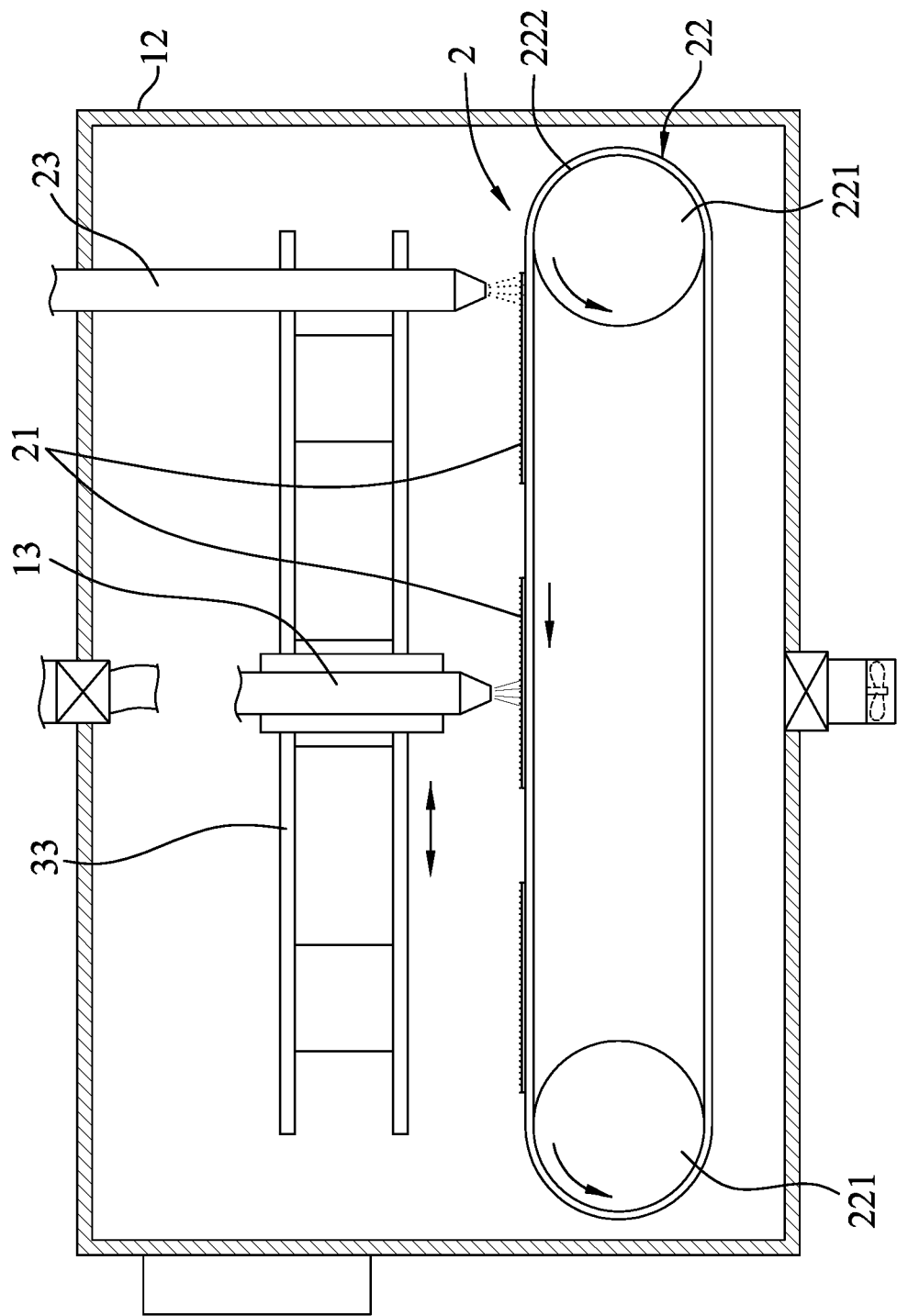
FIG. 10 is a fragmentary schematic diagram illustrating a ninth embodiment of the waste gas purification system according to the disclosure.

Referring to FIG. 10, a ninth embodiment of the waste gas purification system according to the disclosure is similar to the first embodiment, and differs from the first embodiment in the structure of the contaminant capturing apparatus 2 and the way the gas input unit 13 moves. In the ninth embodiment, the drive device 22 further includes a transmission belt 222 that is trained on the rollers 221, and that runs under the gas input unit 13 when the rollers 221 rotate. The contaminant capturing apparatus 2 includes a plurality of capture devices 21 that are sequentially fed to the transmission belt 222, and that move with the transmission belt 222 to sequentially pass under the gas input unit 13 when the rollers 221 rotate. Each of the capture devices 21 is a plate that has a surface having adhesive distributed thereon to adhere the particulate matter in the waste gas. The captures devices 21 are inherently sticky in this embodiment, in which case the adhesive supply device 23 may be omitted, but may be inherently non-sticky in other embodiments, in which case the adhesive supply device 23 would be necessary. In the case where the captures devices 21 are inherently sticky and the adhesive supply device 23 is not omitted, the adhesive supply device 23 supplies adhesive to the surfaces of the capture devices 2, so as to maintain stickiness of the adhesive on the surfaces of the capture devices 21. The gas input unit 13 allows for entrance of the waste gas into the gas container 12 intermittently, and the surfaces of the capture devices 21 are exposed to the waste gas one by one. The driver 33 is configured to drive the gas input unit 13 to move in such a way that a position of a projection of the gas input unit 13 on a surface of the transmission belt 222 is variable, and may be a motorized slide as shown in FIG. 10. It should be noted that the waste gas purification system may further include a feeding apparatus (not shown) for sequentially feeding the capture devices 21 to the transmission belt 222, and a receiving apparatus (not shown) for sequentially receiving the capture devices 21 stained with the particulate matter in the waste gas (i.e., having the particulate matter in the waste gas adhered thereon) from the transmission belt 222. Since the feeding apparatus and the receiving apparatus should be known to one skilled in the art, details thereof are omitted herein for the sake of brevity.

In view of the above, in each of the aforesaid embodiments, since the gas input unit(s) 13 can be driven into movement, the waste gas can be effectively purified.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that the disclosure is not limited to the disclosed embodiments but is intended to cover various arrangements included within the spirit and scope of the broadest interpretation so as to encompass all such modifications and equivalent arrangements.

What is claimed is:

1. A waste gas purification system comprising:
   a gas container;
   a driver;
   a gas input for entrance of waste gas into said gas container, and to be driven by said driver into movement;
   a gas output for discharge of the waste gas out of said gas container after the waste gas is purified; and
   a contaminant capturing apparatus disposed in said gas container, and including a capture device that purifies the waste gas by using an adhesive to adhere particulate matter in the waste gas;
   wherein said contaminant capturing apparatus includes a plurality of said capture devices, said gas input allows for entrance of the waste gas into said gas container intermittently, and respective surfaces of said capture devices are exposed to the waste gas one by one.

2. The waste gas purification system of claim 1, wherein said gas input is driven to move in such a way that a distance therefrom to a surface of a respective capture device is variable.

3. The waste gas purification system of claim 1, wherein said gas input is driven to move in such a way that a position of a projection of said gas input on a surface of a respective capture device is variable.

4. The waste gas purification system of claim 1, wherein said gas input is driven to move in such a way that an angle thereof with respect to a surface of a respective capture device is variable.

5. The waste gas purification system of claim 1, further comprising an exhaust fan that is mounted to said gas output.

6. The waste gas purification system of claim 1, further comprising a device control apparatus that includes an air quality detector and a controller;
  wherein said air quality detector is disposed in said gas container, and is configured to detect an air quality of the waste gas in said gas container and to generate an air quality signal that indicates the air quality of the waste gas;
  wherein said controller is communicatively connected to said air quality detector to receive the air quality signal, is further communicatively connected to said gas input, and is configured to control a gas flow in said gas input based on the air quality of the waste gas as indicated by the air quality signal.

7. The waste gas purification system of claim 1, further comprising a device control apparatus that includes an air quality detector and a controller;
  wherein said air quality detector is disposed in said gas container, and is configured to detect an air quality of the waste gas in said gas container and to generate an air quality signal that indicates the air quality of the waste gas;
  wherein said controller is communicatively connected to said air quality detector to receive the air quality signal, is further communicatively connected to said gas input, and is configured to control operation of said gas input based on the air quality of the waste gas as indicated by the air quality signal.

8. The waste gas purification system of claim 1, wherein said gas input is formed with a plurality of openings that face a surface of a respective capture device.

9. The waste gas purification system of claim 1, comprising a plurality of said gas inputs, wherein each of said gas inputs is formed with an opening through which waste gas enters said gas container, and the openings of said gas inputs face a surface of a respective capture device.

10. The waste gas purification system of claim 1, wherein said gas input is formed with an opening through which waste gas enters said gas container, the waste gas purification system further comprising a reflector that is mounted to said gas input and above said opening of said gas input, and that extends radially-outwardly from said gas input.

11. The waste gas purification system of claim 10, wherein said reflector has a surface that has adhesive distributed thereon to adhere the particulate matter in the waste gas.

12. The waste gas purification system of claim 1, further comprising a device control apparatus that includes an air quality detector and a controller;
  wherein said contaminant capturing apparatus further includes a drive device that is configured to drive said capture devices into continuous movement;
  wherein said air quality detector is disposed in said gas container, and is configured to detect an air quality of the waste gas in said gas container and to generate an air quality signal that indicates the air quality of the waste gas;
  wherein said controller is communicatively connected to said air quality detector to receive the air quality signal, is further communicatively connected to said drive device, and is configured to control said drive device to increase an operation speed of said drive device when the air quality of the waste gas as indicated by the air quality signal is worse than a first predetermined level, and to control said drive device to reduce the operation speed of said drive device when the air quality of the waste gas as indicated by the air quality signal is better than a second predetermined level that represents a better air quality than that represented by the first predetermined level.

13. The waste gas purification system of claim 1, further comprising an environmental parameter control apparatus that includes a temperature control device disposed to adjust the waste gas to having a predetermined temperature before the waste gas enters said gas container through said gas input.

14. The waste gas purification system of claim 1, further comprising an environmental parameter control apparatus that includes a humidity control device disposed to adjust the waste gas to having a predetermined humidity before the waste gas enters said gas container through said gas input.

\* \* \* \* \*